(12) United States Patent
Wechter et al.

(10) Patent No.: US 10,086,207 B2
(45) Date of Patent: Oct. 2, 2018

(54) METHOD AND APPARATUS FOR COMPARING NEUROSTIMULATION PATTERNS

(71) Applicant: Boston Scientific Neuromodulation Corporation, Valencia, CA (US)

(72) Inventors: David Ernest Wechter, San Francisco, CA (US); Rafael Carbunaru, Valley Village, CA (US); Michael A. Moffitt, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 31 days.

(21) Appl. No.: 15/271,316

(22) Filed: Sep. 21, 2016

(65) Prior Publication Data
US 2017/0080242 A1    Mar. 23, 2017

Related U.S. Application Data

(60) Provisional application No. 62/221,432, filed on Sep. 21, 2015.

(51) Int. Cl.
*A61N 1/00*     (2006.01)
*A61N 1/372*    (2006.01)
(Continued)

(52) U.S. Cl.
CPC ....... *A61N 1/37247* (2013.01); *A61N 1/0551* (2013.01); *A61N 1/36132* (2013.01);
(Continued)

(58) Field of Classification Search
CPC .............. A61N 1/36071; A61N 1/3605; A61N 1/36128–1/36185; A61N 1/37242; A61N 1/37241; A61N 1/37247; A61N 1/37264
See application file for complete search history.

(56) References Cited

U.S. PATENT DOCUMENTS 6,662,051 B1    12/2003  Eraker et al.
7,548,786 B2     6/2009  Lee
(Continued)

FOREIGN PATENT DOCUMENTS

WO    WO-2017053340 A1    3/2017

OTHER PUBLICATIONS

Hershey, Bradley Lawrence, et al., "Method and Apparatus for Controlling Temporal Patterns of Neurostimulation", U.S. Appl. No. 15/079,340, filed Mar. 24, 2016.
(Continued)

*Primary Examiner* — Scott Getzow
(74) *Attorney, Agent, or Firm* — Schwegman Lundberg & Woessner, P.A.

(57) ABSTRACT

An example of a system for comparing neurostimulation waveforms can include a user interface configured to receive user input that at least partially defines a first neurostimulation waveform with at least one of differing pulses and differing pulse intervals, where the user input including at least one received parameter of the first neurostimulation waveform. The system can include a storage device configured to store at least one parameter of at least one second neurostimulation waveform, a comparator configured to compare the at least one received parameter of the first neurostimulation waveform to a corresponding at least one parameter of at least one second neurostimulation waveform stored in a memory, the user interface configured to generate and display to the user an indication of a similarity between the compared parameters.

20 Claims, 7 Drawing Sheets

(51) Int. Cl.
   *A61N 1/36* (2006.01)
   *A61N 1/05* (2006.01)
(52) U.S. Cl.
   CPC ..... *A61N 1/36146* (2013.01); *A61N 1/36171* (2013.01); *A61N 1/36175* (2013.01); *A61N 1/36192* (2013.01); *A61N 1/37264* (2013.01)

(56) References Cited

U.S. PATENT DOCUMENTS

| | | |
|---|---|---|
| 7,826,902 B2 | 11/2010 | Stone et al. |
| 2008/0103546 A1 | 5/2008 | Patel et al. |
| 2009/0287271 A1* | 11/2009 | Blum ................ A61N 1/37247 607/45 |
| 2010/0023090 A1 | 1/2010 | Jaax et al. |
| 2010/0222845 A1 | 9/2010 | Goetz |
| 2011/0313483 A1 | 12/2011 | Hincapie Ordonez et al. |
| 2012/0083857 A1 | 4/2012 | Bradley |
| 2013/0289667 A1* | 10/2013 | Wacnik ............. A61N 1/36171 607/72 |
| 2014/0343628 A1 | 11/2014 | Kaula et al. |
| 2015/0235395 A1 | 8/2015 | Ben-oni |
| 2015/0243040 A1 | 8/2015 | Ben-oni et al. |
| 2016/0074662 A1 | 3/2016 | Moffitt et al. |
| 2016/0121126 A1 | 5/2016 | Marnfeldt |
| 2016/0220820 A1 | 8/2016 | Zottola |

OTHER PUBLICATIONS

"International Application Serial No. PCT/US2016/052744, International Search Report dated Dec. 5, 2016", 6 pgs.
"International Application Serial No. PCT/US2016/052744, Written Opinion dated Dec. 5, 2016", 7 pgs.

* cited by examiner

| COMPARE TO LIBRARY - TOP MATCHES ||||
| PATTERN NAME | INSTITUTION / PHYSICIAN | MATCH % | |
| --- | --- | --- | --- |
| DRG STIM | INSTITUTION #1 - DR. GREEN | 95% | HIGHLIGHT DIFFERENCES |
| DHS - 10K | INSTITUTION #2 - DR. BLACK | 92% | HIGHLIGHT DIFFERENCES |
| VENTRAL STIM | INSTITUTION #3 - DR. BROWN | 92% | HIGHLIGHT DIFFERENCES |
| POWER SAVER | DR. MAGENTA | 56% | HIGHLIGHT DIFFERENCES |
| LOW BACK | DR. MAROON | 50% | HIGHLIGHT DIFFERENCES |
| LOWER LIMB | INSTITUTION #4 - DR. RED | 42% | HIGHLIGHT DIFFERENCES |
| ABDOMINAL | INSTITUTION #5 - DR. YELLOW | 2% | HIGHLIGHT DIFFERENCES |

FIG. 8

METHOD AND APPARATUS FOR COMPARING NEUROSTIMULATION PATTERNS

CLAIM OF PRIORITY

This application claims the benefit of priority under 35 U.S.C. § 119(e) of U.S. Provisional Patent Application Ser. No. 62/221,432 to Wechter et al. and filed on Sep. 21, 2015, which is herein incorporated by reference in its entirety.

TECHNICAL FIELD

This document relates generally to medical devices and more particularly to a programming method and apparatus for comparing patterns of electrical stimulation.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and stimulation patterns predetermined at the time of manufacturing may substantially limit the potential for the customization. Such customization may be performed at least in part by a user such as a physician or other caregiver with the patient in a clinical setting.

SUMMARY

Example 1 includes or uses subject matter (e.g., a system, apparatus, article, or the like) for comparing neurostimulation waveforms, comprising: a user interface configured to receive user input that at least partially defines a first neurostimulation waveform with at least one of differing pulses and differing pulse intervals, the user input including at least one received parameter of the first neurostimulation waveform; a storage device configured to store at least one parameter of at least one second neurostimulation waveform; a comparator configured to compare the at least one received parameter of the first neurostimulation waveform to a corresponding at least one parameter of at least one second neurostimulation waveform stored in a memory; and the user interface configured to generate and display to the user an indication of a similarity between the compared parameters.

In Example 2, the system of Example 1 may optionally include a stimulation output circuit configured to generate the first neurostimulation waveform to be delivered by an implantable medical device to an anatomical target of a patient.

In Example 3, the system according to any of the preceding Examples may optionally include at least one controller in communication with the user interface and the storage device, the at least one controller configured to: apply a simulation of the first neurostimulation waveform to at least a portion of an anatomical atlas; and generate to a user an indication of at least one effect on the at least a portion of the anatomical atlas, the user interface configured to display to the user the indication of the at least one effect on the at least a portion of the anatomical atlas.

In Example 4, the system of Example 3, wherein the user interface configured to display to the user the indication of the at least one effect on the at least a portion of the anatomical atlas is configured to: display to the user a graphical representation of an affected region of the anatomical atlas.

In Example 5, the system according to any of Examples 3 and 4, wherein the user interface configured to display to the user the indication of the at least one effect on the at least a portion of the anatomical atlas is configured to: display to the user an indication of at least one type of nerve fiber affected.

In Example 6, the system according to any of Examples 3-5, wherein the at least one controller configured to apply a simulation of the first neurostimulation waveform on at least a portion of an anatomical atlas is configured to: apply a simulation of the first neurostimulation waveform using at least two pre-selected virtual electrodes to at least a portion of an anatomical atlas.

In Example 7, the system according to any of the preceding Examples, wherein the user interface configured to receive user input that at least partially defines a first neurostimulation waveform with at least one of differing pulses and differing pulse intervals is configured to: receive user input that defines at least one of a pulse of the first neurostimulation waveform, at least one pulse interval duration, a pulse group of the first neurostimulation waveform, and a group of pulse groups of the first neurostimulation waveform.

In Example 8, the system according to any of the preceding Examples, wherein the at least one received parameter of the first neurostimulation waveform is selected from the group consisting of an amplitude, pulse width, at least one pulse interval duration, frequency, electrode configurations, total charge injected per unit time, duty cycling, pulse shape, number of phases, phase order, interphase time, charge balance, and ramping.

In Example 9, the system according to any of the preceding Examples, wherein the at least one received parameter includes two or more received parameters, and wherein the user interface is configured to receive user input that selects a subset of the two or more received parameters of the first neurostimulation waveform to compare to a corresponding subset of the two or more received parameters of the at least one second neurostimulation waveform stored in the memory.

Example 10 includes subject matter (such as a method, means for performing acts, machine readable medium including instructions that when performed by a machine cause the machine to performs acts, or an apparatus configured to perform) for comparing neurostimulation waveforms, the method comprising: receiving user input that at least partially defines a first neurostimulation waveform with at least one of differing pulses and differing pulse intervals, the user input including at least one received parameter of the first neurostimulation waveform; comparing the at least one received parameter of the first neurostimulation waveform to a corresponding at least one parameter of at least one second neurostimulation waveform stored in a memory; and generating and displaying to the user an indication of a similarity between the compared parameters.

In Example 11, the method of Example 10, comprising: generating the first neurostimulation waveform to be delivered by an implantable medical device to an anatomical target of a patient.

In Example 12, the method according to any of the preceding Examples, comprising: applying a simulation of the first neurostimulation waveform to at least a portion of an anatomical atlas; and generating and displaying to a user an indication of at least one effect on the at least a portion of the anatomical atlas.

In Example 13, the method of Example 12, wherein generating and displaying to a user an indication of at least one effect on the at least a portion of the anatomical atlas includes: displaying a graphical representation of an affected region of the anatomical atlas.

In Example 14, the method according to any of Examples 12 and 13, wherein generating and displaying to a user an indication of at least one effect on the at least a portion of the anatomical atlas includes: displaying an indication of at least one type of nerve fiber affected.

In Example 15, the method according to any of Examples 12-14, wherein applying a simulation of the first neurostimulation waveform on at least a portion of an anatomical atlas includes: applying a simulation of the first neurostimulation waveform using at least two pre-selected virtual electrodes to at least a portion of an anatomical atlas.

In Example 16, the method according to any of the preceding Examples, wherein receiving user input that at least partially defines a first neurostimulation waveform with at least one of differing pulses and differing pulse intervals includes: receiving user input that defines at least one of a pulse of the first neurostimulation waveform, at least one pulse interval duration, a pulse group of the first neurostimulation waveform, and a group of pulse groups of the first neurostimulation waveform.

In Example 17, the method according to any of the preceding Examples, wherein the at least one received parameter of the first neurostimulation waveform is selected from the group consisting of an amplitude, pulse width, at least one pulse interval duration, frequency, electrode configurations, total charge injected per unit time, duty cycling, pulse shape, number of phases, phase order, interphase time, charge balance, and ramping.

In Example 18, the method according to any of the preceding Examples, wherein the at least one received parameter includes two or more received parameters, the method comprising: receiving user input that selects a subset of the two or more received parameters of the first neurostimulation waveform to compare to a corresponding subset of the two or more received parameters of the at least one second neurostimulation waveform stored in the memory.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 8 is an illustration of an embodiment of a neurostimulation waveform comparison output on a display screen of a GUI.

DETAILED DESCRIPTION

Figure 1:
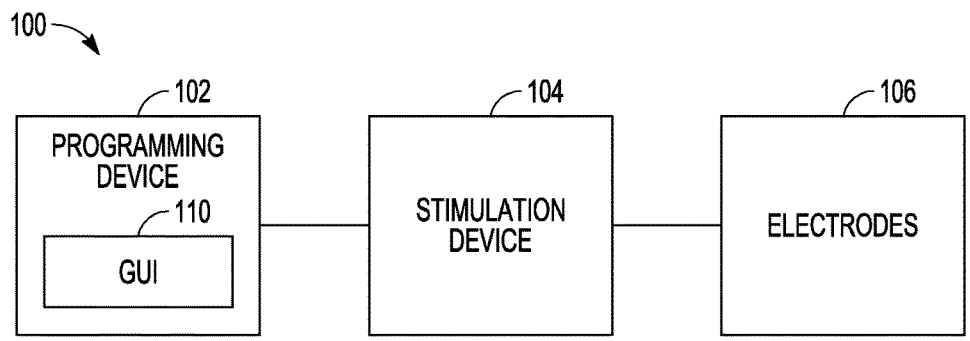
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses various techniques that can allow a user to compare a customized neurostimulation waveform that was not predefined at the time of manufacturing, e.g., that was a result of neurostimulation research, to one or more existing neurostimulation waveforms stored in a repository. The techniques of this disclosure can allow the user the ability to determine whether there may be any benefit to using the customized waveform before that waveform is tested on a subject. If the user determines that one or more compared parameters of the waveforms are sufficiently similar, the user can allow a controller to generate the customized neurostimulation waveform to be delivered by a stimulation device, e.g., an implantable medical device, to an anatomical target of a patient. Also described are techniques that can allow the user to apply a simulation of the customized neurostimulation waveform to an anatomical model to help the user predict if the customized waveform will offer any therapeutic advantages on a particular anatomical target of interest.

The system described in this disclosure allows a user to define the customized neurostimulation waveform. The customized neurostimulation waveform definition can include a pattern of neurostimulation pulses, which includes custom definition of waveforms being the building blocks of the pattern. Such custom definition is achieved by using a graphical user interface (GUI) that makes it possible for the user to perform the custom definition of potentially very complex patterns of neurostimulation pulses by creating and editing graphical representations of relatively simple individual building blocks for each of the patterns. In various embodiments, the individually definable waveforms may include pulses, pulse blocks each including a burst of pulses, pulse trains each including a sequence of pulse blocks, train groups each including a sequence of pulse trains, and neurostimulation programs (also referred to as "programs" in this document) each including one or more train groups scheduled for delivery. A user can define one or more parameters of the customized waveform including, but not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time).

In various embodiments, the present subject matter may be implemented using a combination of hardware and software designed to provide users such as clinical researchers, physicians or other caregivers with the ability to create custom waveforms and patterns in an effort to increase therapeutic efficacy and/or patient satisfaction for neurostimulation therapies, including but not being limited to SCS and DBS therapies. While neurostimulaton is specifically discussed as an example, the present subject matter may apply to any therapy that employs stimulation pulses of electrical or other forms of energy.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device 104 via a wired or wireless link.

In various embodiments, programming device 102 includes a graphical user interface (GUI) 110 that allows the user to set and/or adjust values of the user-programmable parameters by creating and/or editing graphical representations of various waveforms. Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups, as further discussed below. The user may also be allowed to define an electrode selection specific to each individually defined waveform.

As described in more detail below with respect to FIG. 6, the user, e.g., clinical researcher, can input one or more parameters using the GUI 110, for example, that at least partially define a customized first neurostimulation waveform, e.g., that was a result of neurostimulation research. Example parameters that can be of interest include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). The user input can specify that one or more these parameters define at least one of a pulse of the first neurostimulation waveform, a pulse group of the first neurostimulation waveform, and a group of pulse groups of the first neurostimulation waveform, for example.

Figure 6:
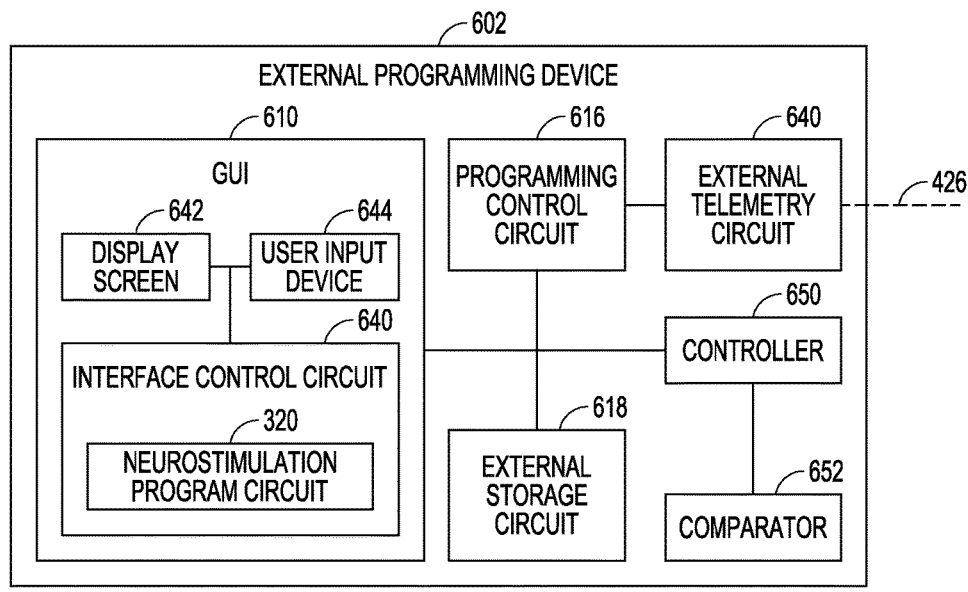
FIG. 6 illustrates an embodiment of an external programming device of an implantable neurostimulation system, such as the external system of FIG. 4.

A controller, e.g., controller 650 of FIG. 6, can retrieve from a storage device, e g., external storage device 618 of FIG. 6, corresponding parameter(s) of a second neurostimulation waveform. Then, a comparator, e.g., comparator 652 of FIG. 6, can compare one or more of the received parameters of the customized first neurostimulation waveform to a corresponding parameter of the second neurostimulation waveform. The GUI 110 can display to the user an indication of a similarity between the compared parameters. The similarity between the compared parameters can allow the user the ability to determine whether there may be any benefit to using the customized waveform before the customized first waveform is tested on a subject, thereby saving time and, in some cases, possible discomfort of the patient. Also described in more detail below with respect to FIG. 6, in some example implementations, the user can apply a simulation of the customized first neurostimulation waveform to an anatomical model to help the user predict if the customized waveform will offer any therapeutic advantages on a particular anatomical target of interest.

Portions of the stimulation device 104, e.g., implantable medical device, or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could include a subcutaneous medical device (e.g., subcutaneous ICD, subcutaneous diagnostic device), wearable medical devices (e.g., patch based sensing device), or other external medical devices.

Figure 2:
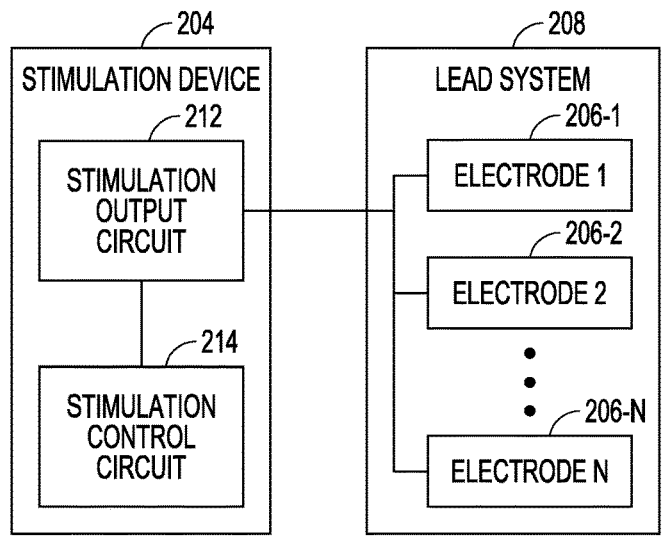
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses, including the user-defined customized neurostimulation waveform received using the GUI 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
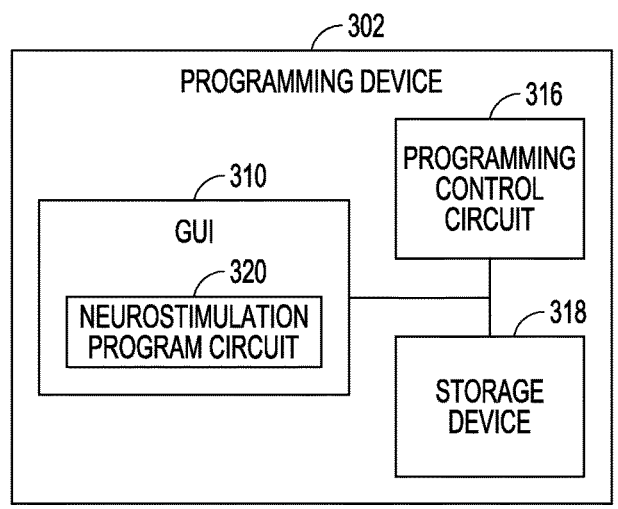
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a GUI 310.

Storage device 318 stores a plurality of individually definable waveforms. For example, storage device 318 can include a collection of existing neurostimulation waveforms, e.g., a "library" or repository of existing neurostimulation waveforms. This collection of waveforms can, for example, be shared by system users, e.g., clinical researches, and a user can upload new neurostimulation waveforms to storage device 318.

Using various techniques of this disclosure, a user can compare parameter(s) of a customized neurostimulation waveform, e.g., received using GUI 310, to corresponding parameter(s) of one or more of the collection of neurostimulation waveforms stored in storage device 318. GUI 310 can then display to the user an indication of a similarity between the compared parameters. The comparison between waveforms is described in more detail below with respect to FIG. 6.

Programming control circuit 316 generates the plurality of stimulation parameters that controls the delivery of the neurostimulation pulses according to the pattern of the neurostimulation pulses. GUI 310 represents an embodiment of GUI 110 and allows the user to define the pattern of the neurostimulation pulses using one or more waveforms selected from the plurality of individually definable waveforms.

In various embodiments, GUI 310 includes a neurostimulation program circuit 320 that creates neurostimulation programs and schedules delivery of the neurostimulation programs. In various embodiments, neurostimulation program circuit 320 allows the user to create each neurostimulation program, including the customized neurostimulation waveform that can be compared with one or more of the neurostimulation waveforms in the library of waveforms in storage device 318, using individually definable waveforms or building blocks such as pulses, pulse blocks each including a burst of pulses, pulse trains each including a sequence of pulse blocks, and train groupings each including a sequence of pulse trains.

In various embodiments, neurostimulation program circuit 320 allows the user to schedule delivery of each neurostimulation program, such as by specifying delivery time for certain building blocks and a frequency at which the program is delivered. In various embodiments, neurostimulation program circuit 320 allows the user to create each building block or program using one or more waveforms stored in storage device 318 as templates. In various embodiments, neurostimulation program circuit 320 allows each newly created building block or program to be saved as additional waveforms stored in storage device 318.

In one embodiment, GUI 310 includes a touchscreen. In various embodiments, GUI 310 includes any type of presentation device, such as interactive or non-interactive screens, and any type of user input device that allows the user to edit the waveforms or building blocks and schedule the programs, such as touchscreen, keyboard, keypad, touchpad, trackball, joystick, and mouse. In various embodiments, circuits of neurostimulation 100, including its various embodiments discussed in this document, may be implemented using a combination of hardware and software. For example, the circuit of GUI 100, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
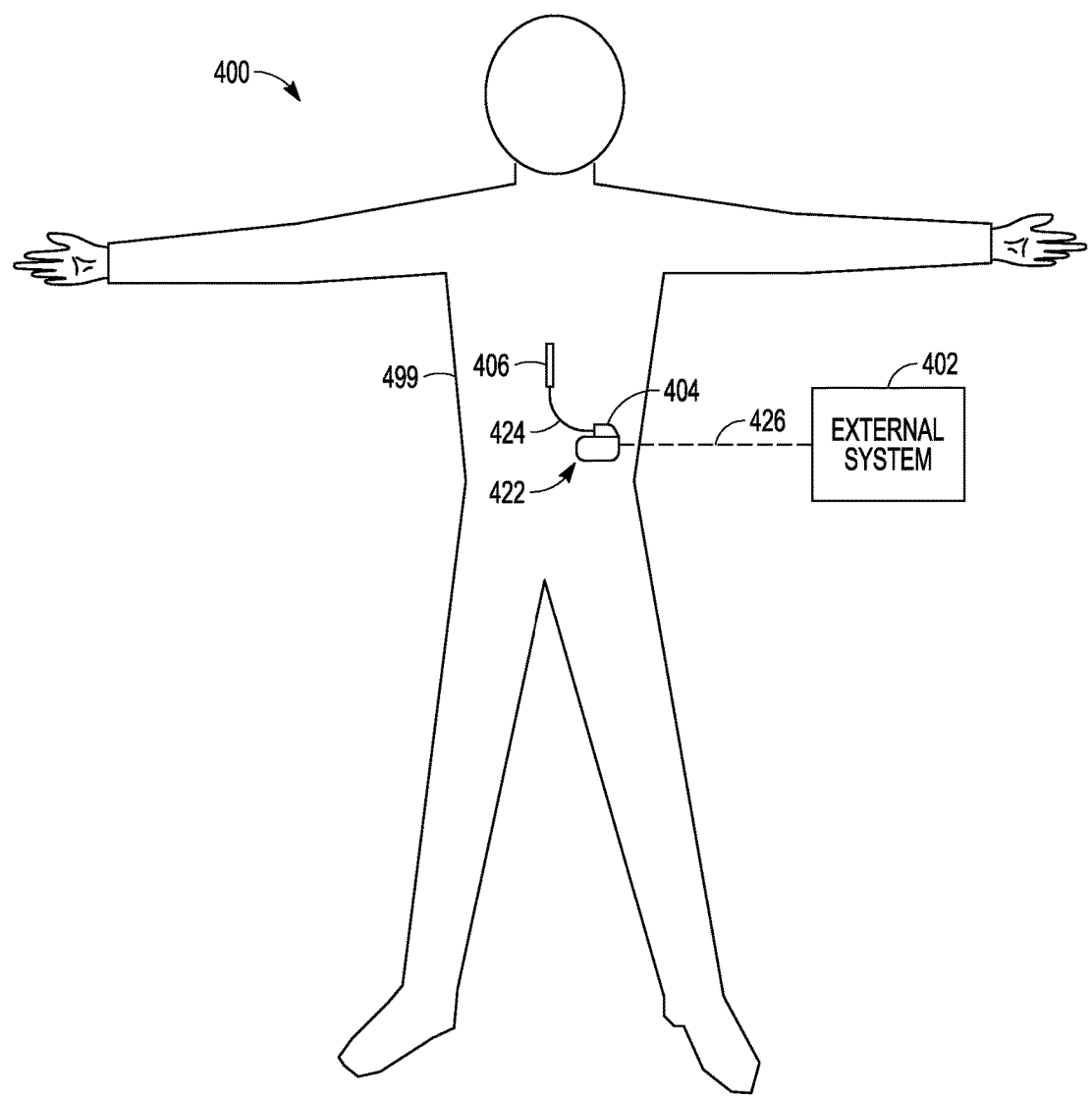
FIG. 4 illustrates an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in the patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302. In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

Figure 5:
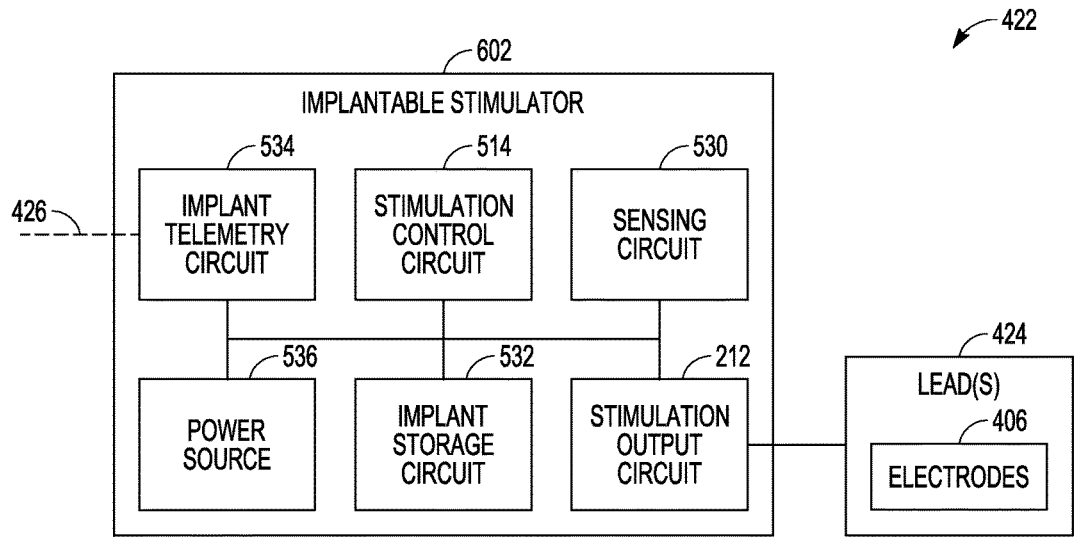
FIG. 5 illustrates an embodiment of an implantable stimulator and one or more leads of an implantable neurostimulation system, such as the implantable system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation.

Stimulation output circuit 212 is electrically connected to electrodes 406 through lead 424, and delivers each of the neurostimulation pulses through a set of electrodes selected from electrodes 406. Stimulation output circuit 212 can generate and deliver the customized first neurostimulation waveform (input by the user and compared to existing neurostimulation waveforms) to an anatomical target of a patient.

Stimulation control circuit 514 represents an embodiment of stimulation control circuit 214 and controls the delivery of the neurostimulation pulses using the plurality of stimulation parameters specifying the pattern of the neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters. Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

FIG. 6 illustrates an embodiment of an external programmer 602 of an implantable neurostimulation system, such as external system 402. External programmer 602 represents an embodiment of programming device 302, and includes an external telemetry circuit 640, an external storage device 618, a programming control circuit 616, a GUI 610, a controller 650, and a comparator 652.

External telemetry circuit 640 provides external programmer 602 with wireless communication with another device such as implantable stimulator 404 via telemetry link 426, including transmitting the plurality of stimulation parameters to implantable stimulator 404. In one embodiment, external telemetry circuit 640 also transmits power to implantable stimulator 404 through the inductive couple.

External storage device 618 stores a plurality of existing neurostimulation waveforms, including individually definable waveforms each selectable for use as a portion of the pattern of the neurostimulation pulses. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 618 can be definable at least in part by one or more parameters including, but not limited to the following: amplitude, pulse width, frequency, electrode configurations, total charge injected per unit time, cycling (e.g., on/off time), pulse shape, number of phases, phase order, interphase time, charge balance, and ramping.

External storage device 618 also stores a plurality of individually definable fields. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, based on the pattern of the neurostimulation pulses. The pattern is defined using one or more waveforms selected from the plurality of individually definable waveforms stored in external storage device 618. In various embodiment, programming control circuit 616 checks values of the plurality of stimulation parameters against safety rules to limit these values within constraints of the safety rules. In one embodiment, the safety rules are heuristic rules.

GUI 610 represents an embodiment of user interface 310 and allows the user to define the pattern of neurostimulation pulses and perform various other monitoring and programming tasks. GUI 610 includes a display screen 642, a user input device 644, and an interface control circuit 640. Display screen 642 may include any type of interactive or non-interactive screens, and user input device 644 may include any type of user input devices that supports the various functions discussed in this document, such as touchscreen, keyboard, keypad, touchpad, trackball, joystick, and mouse. In one embodiment, GUI 610 includes an interactive screen that displays a graphical representation of a stimulation waveform and allows the user to adjust the waveform by graphically editing the waveform and/or various building blocks of the waveform. GUI 610 may also allow the user to perform any other functions discussed in this document where graphical editing is suitable as may be appreciated by those skilled in the art.

Interface control circuit 640 controls the operation of GUI 610 including responding to various inputs received by user input device 644 and defining the one or more stimulation waveforms. Interface control circuit 640 includes neurostimulation control circuit 320.

In various embodiments, external programming device 602 has operation modes including a composition mode and a real-time programming mode. Under the composition mode (also known as the pulse pattern composition mode), GUI 610 is activated, while programming control circuit 616 is inactivated. Programming control circuit 616 does not dynamically update values of the plurality of stimulation parameters in response to any change in the one or more stimulation waveforms. Under the real-time programming mode, both GUI 610 and programming control circuit 616 are activated. Programming control circuit 616 dynamically updates values of the plurality of stimulation parameters in response to changes in the set of one or more stimulation waveforms, and transmits the plurality of stimulation parameters with the updated values to implantable stimulator 404.

The controller 650 can be a microprocessor that communicates with the external telemetry circuit 640, the external storage device 618, the programming control circuit 616, the GUI 610, the comparator 652 via a bidirectional data bus. The controller 650 can be implemented by other types of logic circuitry (e.g., discrete components or programmable logic arrays) using a state machine type of design. As used in this disclosure, the term "circuitry" should be taken to refer to either discrete logic circuitry, firmware, or to the programming of a microprocessor. The comparator 652 can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

In accordance with various techniques of this disclosure, a user can input for comparison a customized neurostimulation waveform, e.g., that was a result of neurostimulation research, to one or more existing neurostimulation waveforms stored in a repository, e.g., in external storage device 618, to determine whether there may be any benefit to using the customized waveform before that waveform is tested on a subject. The controller 650 can receive, via GUI 610 for example, user input that at least partially defines a customized neurostimulation waveform with at least one of differing pulses and differing pulse intervals.

The customized neurostimulation waveform definition can include a pattern of neurostimulation pulses, which includes custom definition of waveforms being the building blocks of the pattern. The customized neurostimulation waveform can include pulses, pulse blocks each including a burst of pulses, pulse trains each including a sequence of pulse blocks, train groups each including a sequence of pulse trains, and neurostimulation programs (also referred to as "programs" in this document) each including one or more train groups scheduled for delivery. A pulse interval can include a duration between successive pulses, successive pulse blocks, successive pulse trains, and/or successive train groups during which the IMD is not delivering stimulation.

The user input can include one or more parameters of the neurostimulation waveform that can be compared to corresponding parameter(s) of a second (or more) neurostimulation waveform with at least one of differing pulses and differing pulse intervals stored in a memory, e.g., external storage device 618. For example, a user can define one or more parameters of the customized waveform including, but not limited to the following: amplitude, pulse width, at least one pulse interval duration, frequency, electrode configurations, total charge injected per unit time, cycling (e.g., on/off time), pulse shape, number of phases, phase order, interphase time, charge balance, and ramping.

After having received the user input defining the customized neurostimulation waveform, the controller 650 can retrieve from the external storage device 618 one or more existing neurostimulation waveforms and compare the existing waveform(s) to the received customized neurostimulation waveform using comparator 652. For example, the comparator 652 can compare one or more of the received parameters of the customized first neurostimulation waveform to a corresponding parameter of the second neurostimulation waveform. The GUI 110 can display to the user an indication of a similarity between the compared parameters. In this manner, the user can review, for example, any variations in amplitude, pulse width, at least one pulse interval duration, frequency, total charge injected per unit time, cycling (e.g., on/off time), pulse shape, number of phases, phase order, interphase time, charge balance, ramping, as well as spatial variance (e.g., electrode configuration changes over time) between the customized neurostimulation waveform and the existing waveforms stored in the external storage device 618. The indication of similarity between the compared parameters can allow the user the ability to determine whether there may be any benefit to using the customized waveform before the customized first waveform is tested on a subject, thereby saving time and, in some cases, possible discomfort of the patient.

In an example implementation, the user can define a neurostimulation waveform having one or more parameters and specify which of the one or more parameters should be compared to the existing waveforms or, if all the parameters are to be compared, which of the compared parameters should be displayed to the user. By way of specific example, the user may be most interested in amplitude variation and may specify that comparator 652 compare only the amplitude of the inputted neurostimulation waveform to the amplitudes of existing waveforms. The comparator 652 can compare the selected parameter, e.g., amplitude, of the inputted waveform with the corresponding parameter, e.g., amplitude, of the one or more existing waveforms. The comparator 652 can then output to the controller 650 the results of the comparison between the compared parameters, e.g., amplitudes. The controller 650 can then generate and display to the user an indication of a similarity between the compared parameters.

As an example of an indication of a similarity between the compared parameters, the controller 650 can cause GUI 610 to display a percentage difference, e.g., 5% difference, or a percentage match, e.g., 95% match, between the amplitudes. As another example an indication of a similarity between the compared parameters, the controller 650 can cause GUI 610 to display a magnitude difference, e.g., 0.5 millivolts, between the amplitudes. An example output on a display is shown and described below with respect to FIG. 8.

In some example implementations, differences between the waveform parameters can be displayed, e.g., highlighted, on the GUI 610. If the user determines that the compared parameters are sufficiently similar, the user can allow the controller 650 to generate the customized neurostimulation waveform to be delivered by a stimulation device 404 (FIG. 4), e.g., an implantable medical device, to an anatomical target of a patient.

By way of another specific example, the user may be most interested in two parameters, e.g., amplitude and frequency variation, and may specify that comparator 652 compare only the amplitude and frequency of the inputted neurostimulation waveform to the amplitudes and frequencies of existing waveforms (or compare all the parameters and display only the specified parameters, e.g., amplitude and frequency variations). For example, the user may input, e.g. via GUI 610, a plurality of parameters of the customized neurostimulation waveform, and then select a subset of those parameters, e.g., amplitude and frequency, of the first neurostimulation waveform to compare to a corresponding subset of parameters of the neurostimulation waveform(s) stored in the memory The comparator 652 can compare the selected parameters, e.g., amplitude and frequency, of the inputted waveform with the corresponding parameters, e.g., amplitude and frequency, of the one or more existing waveforms. The comparator 652 can then output to the controller 650 the results of the comparison between the compared parameters. The controller 650 can generate and display to the user an indication of a similarity using the comparison between the compared parameters. As an example, the controller 650 can cause GUI 610 to display a percentage difference, percentage, match, or magnitude difference between the amplitude and the frequency, e.g., in two columns on the display. If the user determines that the compared parameters are sufficiently similar, the user can allow the controller 650 to generate the customized neurostimulation waveform to be delivered by a stimulation device 404 (FIG. 4), e.g., an implantable medical device, to an anatomical target of a patient.

In some example implementations, the comparator 652 can compare more than two of the inputted parameters, e.g., each of the N-number of inputted parameters, to the corresponding parameters of the second neurostimulation waveform. The comparator 652 can then output to the controller 650 the results of the comparison between the compared parameters. The controller 650 can then generate and display to the user an indication of a similarity between the compared parameters. As an example, the controller 650 can cause GUI 610 to percentage difference, percentage, match, or magnitude difference between the parameters, e.g., in multiple columns on the display, using a filter with a drop-down list, and the like.

In examples in which the user is interested in comparing two or more parameters of the customized neurostimulation waveform against corresponding parameters of existing neurostimulation waveforms, e.g., stored in external storage device 618, the user can specify a weighting factor to apply to one (or more) of the waveform parameters to weight the specified parameter(s) more heavily than the other parameters, e.g., using a positive weighting factor. Alternatively, the weighting factor can be used to weight the specified parameter less heavily than the other parameters, e.g., using a negative weighting factor.

In some example implementations, the weighting factor can be user-defined. In other example implementations, the weighting factor can be a default weighting factor. By way of specific example, a user may be interested in comparing the amplitude and pulse width parameters of the customized waveform but most interested in amplitude. As such, the user can specify that the comparator 652 apply a weighting factor to the amplitude parameter of the existing waveform(s) during its comparison to weight the amplitude parameter more heavily.

In various example implementations, the user or the controller 650 can define a window within which the comparator 652 can compare the waveforms, e.g., a first customized neurostimulation waveform input by the user and at least one second existing neurostimulation waveform stored in external storage device 618. In some example implementations, the window can be defined, e.g., by the user, in the time domain to compare the customized neurostimulation waveform to one or more existing neurostimulation waveforms.

In an example implementation of a comparison using a time domain window, the user may input a specific duration of the window for comparison between the waveforms, e.g., 0.25 seconds to 10 minutes. By way of specific example and using the amplitude parameter only for purposes of illustration, the comparator 652 can determine an average (or other central tendency) of the amplitude for each of the one or more existing waveforms over a specified (either by the user or by default) duration, e.g., 30 seconds. The comparator 652 can then compare the determined average (or other central tendency) to the amplitude of the user inputted waveform over the specified duration. In an example output, the controller 650 can display on the GUI 610 an indication of a running average difference over time between the user inputted waveform and the existing waveforms.

In other example implementations, the window can be defined (either by the user or as a default) in terms of the number of pulses, pulse groups, and groups of pulse groups, for example. By way of specific example and using the amplitude parameter only for purposes of illustration, the user can specify a window of 50 pulses for the comparison between waveforms. The comparator 652 can determine an average (or other central tendency) of the amplitude for each of the one or more existing waveforms over the specified pulse duration, e.g., 50 pulse. The comparator 652 can then compare the determined average (or other central tendency) to the amplitude of the user inputted waveform over the specified duration. In an example output, the controller 650 can display on the GUI 610 an indication of a running average difference between the user inputted waveform and the existing waveforms over the defined length of pulses.

In addition to pulse-based and time-based windows, the user can specify that the comparator 652 compare the user-inputted waveform and the existing waveforms in the frequency-domain.

As indicated above, the customized neurostimulation waveform can be defined by phase-related parameters including the number of phases, the phase order, and interphase time. In some example implementations, to compare the customized neurostimulation waveform to the existing waveform(s), the controller 650 can compensate for any phase offset between the waveforms, e.g., by shifting the customized waveform.

Other example techniques for determining an indication of similarity between the customized neurostimulation waveform and the existing waveform(s) can include correlation-based similarity techniques including, but not limited to, using a Pearson correlation to generate a similarity score that can be displayed to the user.

In some example implementations, the comparator 652 can use a threshold, e.g., default or user-specified, when comparing the one or more received parameters of the customized neurostimulation waveform to the corresponding one or more parameters of the neurostimulation waveform(s) stored in a memory device, e.g., external storage device 618. For example, a user may want to consider any compared parameters as sufficiently "matching" when those parameters differ by an amount equal to or less than a threshold, e.g., user specified or default. As an example, the user may specify that if the percentage match of a corresponding compared parameter(s) is greater than 98%, the parameter can be displayed as a match, e.g. using GUI 610. In an example implementation, the user can input the threshold using GUI 610, and following a comparison by the comparator 652 between the customized neurostimulation waveform and the stored waveform(s), the comparator 652 can then compare the variation (if any) between the parameters to the threshold. If the comparison is less than the threshold, for example, the parameter can be displayed as a match.

As mentioned above, in some example implementations, the controller 650 can apply a simulation of the customized neurostimulation waveform to an anatomical model or atlas stored in the external storage device 618, e.g., a common anatomical atlas for a plurality of patients of a patient population or a patient-specific anatomical atlas, to help the user predict if the customized waveform will offer any therapeutic advantages on a particular anatomical target of interest. For example, the simulation can provide feedback to the user on how the inputted customized neurostimulation waveform will affect a particular neural network, e.g., spinal cord, region of the brain, etc.

In some example implementations, the controller 650 can generate and display to the user an indication of at least one effect of the applied simulation, e.g., on a portion of the anatomical atlas. For example, the controller 650 can generate and display on the display screen 642 the output of the simulation in the form of graphical anatomical representation of a desired target with any affected portions highlighted, e.g., dorsal horn of the spinal cord. As another example, the controller 650 can generate and display on the display screen 642 an indication of type(s) of nerve fibers affected by the applied simulation, e.g., A-beta fibers, A-delta fibers, C-type fibers, etc.

As mentioned above, spatial variance, e.g., electrode configuration changes over time, between the customized neurostimulation and the existing waveforms may be of interest to a user. If spatial variance is not of interest, however, it may be desirable in some example implementations to reduce or eliminate the spatial aspect of the customized neurostimulation waveform input by the user when applying a simulation of the customized neurostimulation waveform to at least a portion of an anatomical atlas. For example, to reduce or eliminate the spatial aspect between electrode configurations, the controller 650 can apply the simulation to the anatomical atlas using two (or more) pre-selected virtual electrodes, e.g., user-defined or default, in order to generate a generic spatial field for the anatomical simulation. The pre-selected virtual electrodes can include at least one virtual electrode defined as an anode and at least one virtual electrode defined as a cathode for purposes of the simulation.

It should be noted that the indication of the at least one effect of the applied simulation need not be a graphical representation. Rather, the effect(s) can be displayed as text, for example, on the display 642, or as combination of text and graphics. Additionally, the results of the simulation can be output in a format for sharing with other clinicians, researchers, or employees, for example. For example, if a clinician tries a neurostimulation program that has beneficial effects in a clinical setting, it may be desirable to export the program parameters and other information, e.g., to other clinicians, members of a company, or an academic research group, to help ascertain why certain parameters were beneficial.

Figure 7:
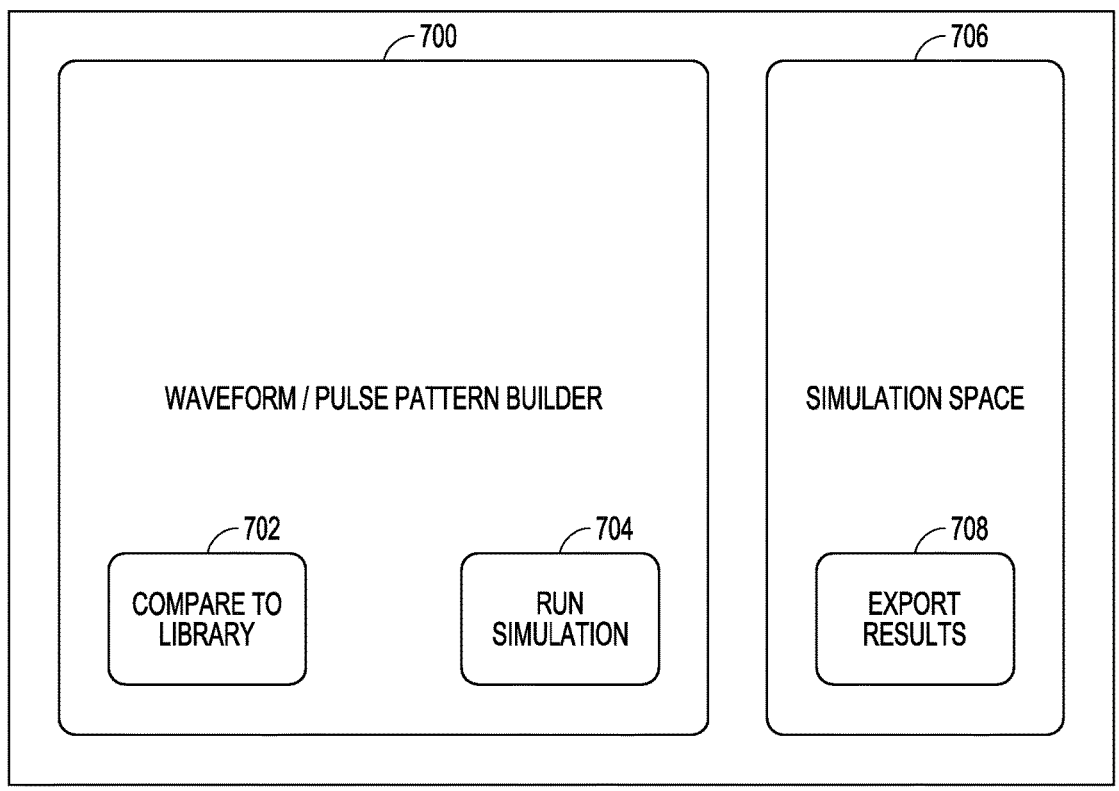
FIG. 7 is an illustration of an embodiment of a neurostimulation waveform builder on a display screen of a graphical user interface (GUI).

FIG. 7 is an illustration of an embodiment of a neurostimulation waveform/pulse pattern builder 700 on a display screen of a GUI, such as on display screen 642 of GUI 610. Example systems for programming or "building" neurostimulation waveform and pulse patterns are described in the following commonly assigned U.S. Provisional Patent Application Numbers, the entire contents of each being incorporated herein by reference: U.S. Provisional Patent Application No. 62/111,715, titled "METHOD AND APPARATUS FOR PROGRAMMING CHARGE RECOVERY IN NEUROSTIMULATION WAVEFORM," to Dennis Zottola and filed on Feb. 4, 2015; U.S. Provisional Patent Application No. 62/137,567, titled "METHOD AND APPARATUS FOR CONTROLLING TEMPORAL PATTERNS OF NEUROSTIMULATION," to Bradley Hershey et al. and filed on Mar. 24, 2015; U.S. Provisional Patent Application No. 62/050,505, titled "GRAPHICAL USER INTERFACE FOR PROGRAMMING NEUROSTIMULATION PULSE PATTERNS," to Michael Moffitt et al. and filed on Sep. 15, 2014; and U.S. Provisional Patent Application No. 62/075,079, titled "METHOD AND APPARATUS FOR PROGRAMMING COMPLEX NEUROSTIMULATION PATTERNS," to Goran Marnfeldt and filed on Nov. 4, 2014.

Using the waveform builder 700, which can use neurostimulation program circuit 320 of FIG. 3 to create the waveform, for example, a user can input one or more parameters that at least partially define the customized neurostimulation waveform, including, but not limited to the following: amplitude, pulse width, at least one pulse interval duration, frequency, total charge injected per unit time, cycling (e.g., on/off time), pulse shape, number of phases, phase order, interphase time, charge balance, ramping, as well as spatial variance (e.g., electrode configuration changes over time). The user input can specify that these parameters define at least one of a pulse of the first neurostimulation waveform, at least one pulse interval duration, a pulse group of the first neurostimulation waveform, and a group of pulse groups of the first neurostimulation waveform, for example.

In the illustrated example in FIG. 7, the builder 700 includes a Compare to Library button 702 and, in some example implementations, a Run Simulation button 704. The Compare to Library button 702 allows for the controller 650 (FIG. 6) to retrieve from the external storage device 618 (FIG. 6) one or more existing neurostimulation waveforms and, using comparator 652 (FIG. 6), compare the existing waveform(s) to the received customized neurostimulation waveform. An example output is depicted in FIG. 8. For brevity, the comparison details described in detail above will not be described again.

In example configurations that include the Run Simulation button 704, the Run Simulation button 704 allows the controller 650 to apply a simulation of the customized neurostimulation waveform to an anatomical model or atlas stored in the external storage device 618 (FIG. 6) to help the user predict if the customized waveform will offer any therapeutic advantages on a particular anatomical target of interest.

Figure 9:
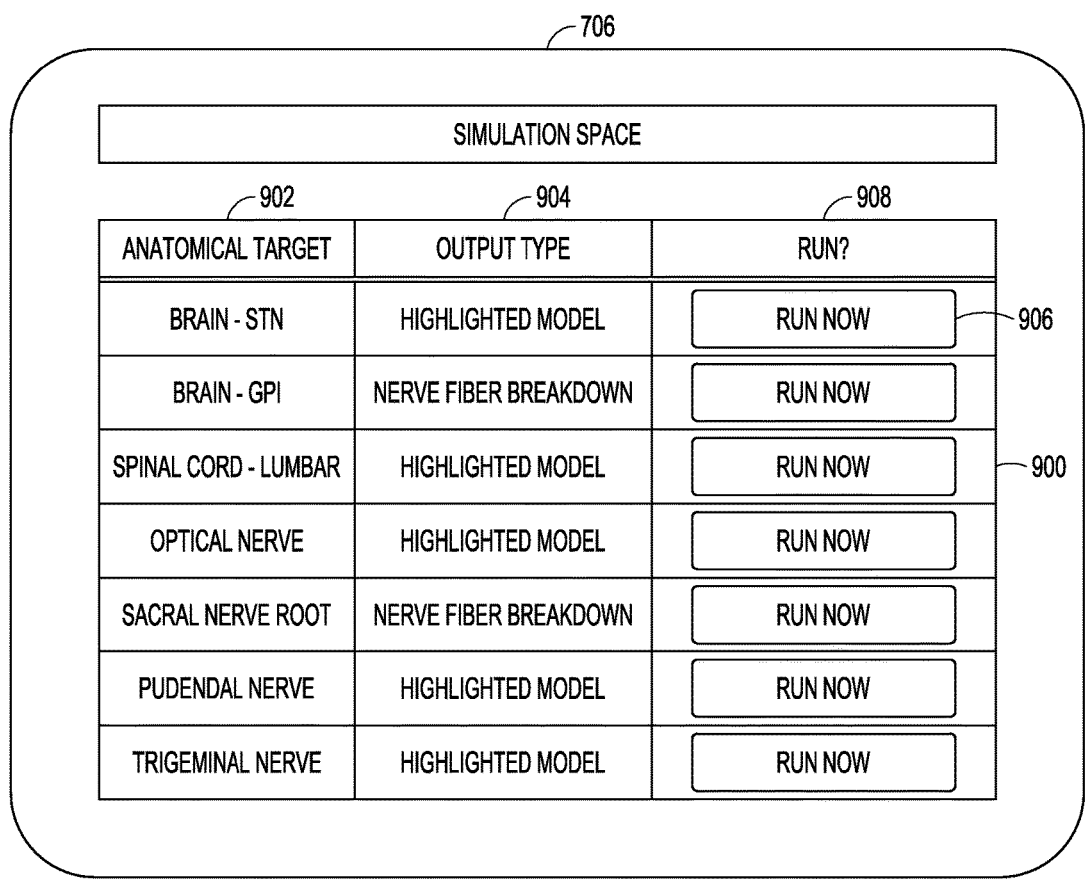
FIG. 9 is an illustration of an embodiment of a neurostimulation waveform simulation space on a display screen of a GUI.

The simulation of the customized neurostimulation waveform can be applied to the anatomical model or atlas and displayed in Simulation Space 706 on the display screen 642 of GUI 610 (FIG. 6). The controller 650 (FIG. 6) can generate and display to the user an indication of at least one effect of the applied simulation, e.g., on a portion of the anatomical atlas. For example, the controller 650 can generate and display in the Simulation Space 706 the output of the simulation in the form of graphical anatomical representation of a desired target with any affected portions highlighted, e.g., dorsal horn of the spinal cord. As another example, the controller 650 can generate and display on the display screen 642 an indication of type(s) of nerve fibers affected by the applied simulation, e.g., A-beta fibers, A-delta fibers, and C-type fibers, etc. An example output is depicted in FIG. 9.

In some example implementations, the Simulation Space 706 can include an Export Results button 708 that can output the results of the simulation in a format for sharing with other clinicians, researchers, or employees, for example.

FIG. 8 is an illustration of an embodiment of a neurostimulation waveform comparison output 800 on a display screen of a GUI, such as on display screen 642 of GUI 610. In some examples, the comparison output space 800 can display the top matches, e.g., a user-specified or default value, that resulted from the comparison between the customized neurostimulation waveform input by the user and the one or more existing waveforms stored in the library of waveforms in external storage device 618 (FIG. 6) for example.

In some examples, the comparison output can be displayed in columns, such as shown in FIG. 8. For example, a left-hand column 802 can display a pattern name, a middle column 804 can display the name of the institution and/or physician that created, uploaded, or otherwise stored the pattern in the library, and a right-hand column 806 can display the results of the comparison. In the particular example implementation shown in FIG. 8, a percentage match is shown, e.g., 95%. In other example implementations, a percentage difference, e.g., 5%, or magnitude difference, e.g., 0.5 millivolts, can be displayed.

In some examples, the right-hand column 806 can itself include multiple columns that each display a percentage match, for example, of corresponding compared parameters. In other example implementations, the right-hand column 806 can include a filter with a drop-down list, for example, so that the user can select one or more parameters of interest to be displayed.

The comparison output 800 can also include a highlight differences button 808 that allows a user to view a detailed comparison of the particular pattern displayed in column 802 and the customized neurostimulation waveform of interest to the user. For example, the highlight differences button 808 can cause the controller 650 (FIG. 6) to display side-by-side comparisons of corresponding parameters.

If the user determines that the compared parameters are sufficiently similar, the user can allow the controller 650 to generate the customized neurostimulation waveform to be delivered by a stimulation device 404 (FIG. 4), e.g., an implantable medical device, to an anatomical target of a patient.

FIG. 9 is an illustration of an embodiment of a neurostimulation waveform Simulation Space 706 (FIG. 7) on a display screen of a GUI, such as on display screen 642 of GUI 610. In some examples, the Simulation Space 706 can display a table 900 that includes one or more anatomical targets 902 with a corresponding user-selected output type 904, e.g., "highlighted model" and/or "nerve fiber breakdown." As described above, the output types 904 can include, for example, displaying in Simulation Space 706 a graphical anatomical representation of a desired target with any affected portions highlighted, e.g., Brain STN, Spinal Cord—Lumbar, Occipital Nerve, etc. As another example, the controller 650 can generate and display on the display screen 642 an indication of type(s) of nerve fibers affected by the applied simulation, e.g., A-beta fibers, A-delta fibers, and C-type fibers, etc. The Run Now button 906 in Run column 908 allows the controller 650 (FIG. 6) to apply a simulation of the customized neurostimulation waveform to an anatomical model or atlas stored in the external storage device 618, e.g., a common anatomical atlas for a plurality of patients of a patient population or a patient-specific anatomical atlas. The controller 650 (FIG. 6) can then display the output of the simulation within the Simulation Space 706.

Figure 10:
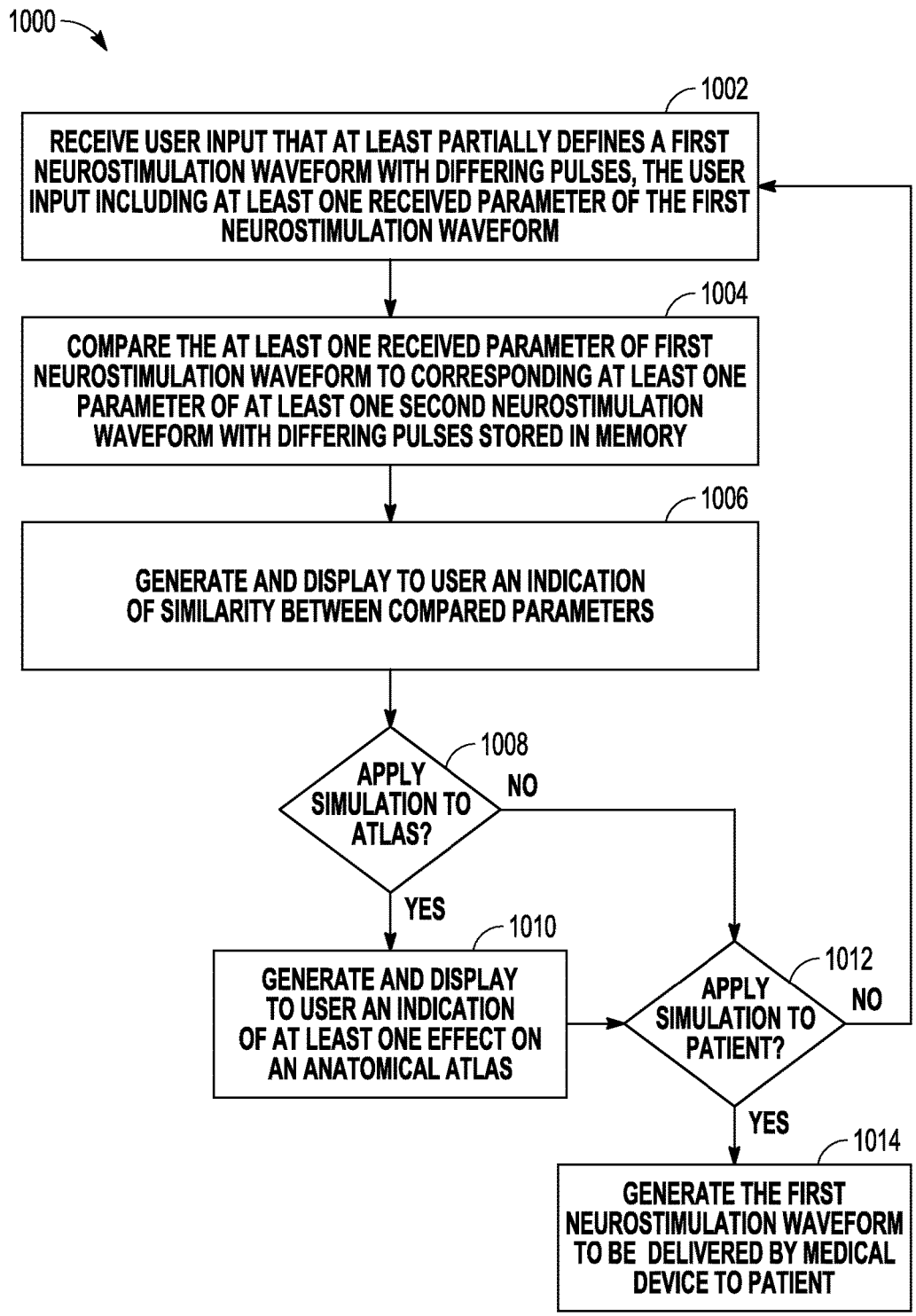
FIG. 10 illustrates an example of a method for comparing neurostimulation waveforms.

FIG. 10 illustrates an example of a method for comparing neurostimulation waveforms. In an example, the method 1000 can be performed using system 100, including various embodiments of its components as discussed in this document. For example, the external programming device 602 (FIG. 6) and implantable stimulator 404 (FIG. 5) can be configured to performing one or more acts of method 1000.

At 1002, a user interface, e.g., GUI 640, can receive user input via waveform builder 700 of FIG. 7 that at least partially defines a first neurostimulation waveform with at least one of differing pulses and differing pulse intervals, the user input including at least one received parameter of the first neurostimulation waveform. As indicated above, parameters of interest include, but are not limited to the following: amplitude, pulse width, at least one pulse interval duration, frequency, electrode configurations, total charge injected per unit time, cycling (e.g., on/off time), pulse shape, number of phases, phase order, interphase time, charge balance, and ramping.

At 1004, a compare waveforms command is received from the user using the GUI, e.g., compare to library button 702 of FIG. 7. In response, a controller, e.g., controller 650 of FIG. 6, can retrieve from a storage device, e g., external storage device 618 of FIG. 6, corresponding parameter(s) of a second neurostimulation waveform. Then, a comparator, e.g., comparator 652 of FIG. 6, can compare one or more of the received parameters of the customized first neurostimulation waveform to a corresponding parameter of the second neurostimulation waveform.

At 1006, the controller can cause the user interface to generate and display to the user, e.g., using waveform comparison output 800 on a display screen, an indication of a similarity between the compared parameters. The similarity between the compared parameters can allow the user the ability to determine whether there may be any benefit to using the customized waveform before the customized first waveform is tested on a subject, thereby saving time and, in some cases, possible discomfort of the patient.

Optionally and as shown at 1008, in some example implementations, the user can apply a simulation of the customized first neurostimulation waveform to an anatomical model to help the user predict if the customized waveform will offer any therapeutic advantages on a particular anatomical target of interest. If a run simulation command is received, e.g., using the Run Simulation button 704 of FIG. 7, ("YES" branch of 1008), then the controller can apply a simulation of the first neurostimulation waveform to at least a portion of an anatomical atlas and generate to a user an indication of at least one effect on the at least a portion of the anatomical atlas, and the user interface can display to the user, e.g., in Simulation Space 706, the indication of the at least one effect on the at least a portion of the anatomical atlas (block 1010).

If the user decides not to apply a simulation of the customized neurostimulation waveform to the anatomical atlas ("NO" branch of block 1008) or, after having reviewed the indication of the effect of the applied simulation on the anatomical atlas (block 1010), the user can decide whether to apply the customized neurostimulation waveform to a patient (block 1012). If the user decides that stimulation is to be applied ("YES" branch of block 1012), a controller can generate the customized neurostimulation waveform to be delivered by a stimulation device, e.g., an implantable medical device, to an anatomical target of a patient (block 1014). If the user decides that stimulation is not to be applied ("NO" branch of block 1012), the method can begin back at block 1002 and wait for user input that defines another customized waveform.

VARIOUS NOTES AND EXAMPLES

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for comparing neurostimulation waveforms, the method comprising:
   receiving user input that at least partially defines a first neurostimulation waveform with at least one of differing pulses and differing pulse intervals, the user input including at least one received parameter of the first neurostimulation waveform;
   comparing the at least one received parameter of the first neurostimulation waveform to a corresponding at least one parameter of at least one second neurostimulation waveform stored in a memory;
   generating and displaying to the user an indication of a similarity between the compared parameters;
   applying a simulation of the first neurostimulation waveform using at least two pre-selected virtual electrodes to at least a portion of an anatomical atlas; and
   generating and displaying to a user an indication of at least one effect on the at least a portion of the anatomical atlas.

2. The method of claim 1, comprising:
   generating the first neurostimulation waveform to be delivered by an implantable medical device to an anatomical target of a patient.

3. The method of claim 1, wherein generating and displaying to a user an indication of at least one effect on the at least a portion of the anatomical atlas includes:
   displaying a graphical representation of an affected region of the anatomical atlas.

4. The method of claim 1, wherein generating and displaying to a user an indication of at least one effect on the at least a portion of the anatomical atlas includes:
   displaying an indication of at least one type of nerve fiber affected.

5. The method of claim 1, wherein receiving user input that at least partially defines a first neurostimulation waveform with at least one of differing pulses and differing pulse intervals includes:
   receiving user input that defines at least one of a pulse of the first neurostimulation waveform, at least one pulse interval duration, a pulse group of the first neurostimulation waveform, and a group of pulse groups of the first neurostimulation waveform.

6. The method of claim 1, wherein the at least one received parameter of the first neurostimulation waveform is selected from the group consisting of an amplitude, pulse width, at least one pulse interval duration, frequency, electrode configurations, total charge injected per unit time, duty cycling, pulse shape, number of phases, phase order, interphase time, charge balance, and ramping.

7. The method of claim 1, wherein the at least one received parameter includes two or more received parameters, the method comprising:
   receiving user input that selects a subset of the two or more received parameters of the first neurostimulation waveform to compare to a corresponding subset of the two or more received parameters of the at least one second neurostimulation waveform stored in the memory.

8. A system for comparing neurostimulation waveforms, comprising:
- a user interface configured to receive user input that at least partially defines a first neurostimulation waveform with at least one of differing pulses and differing pulse intervals the user input including at least one received parameter of the first neurostimulation waveform;
- a storage device configured to store at least one parameter of at least one second neurostimulation waveform;
- a comparator configured to compare the at least one received parameter of the first neurostimulation waveform to a corresponding at least one parameter of at least one second neurostimulation waveform stored in a memory;
- the user interface configured to generate and display to the user an indication of a similarity between the compared parameters; and
- at least one controller in communication with the user interface and the storage device, the at least one controller configured to:
  - apply a simulation of the first neurostimulation waveform using at least two pre-selected virtual electrodes to at least a portion of an anatomical atlas; and
  - generate to a user an indication of at least one effect on the at least a portion of the anatomical atlas,
- the user interface configured to display to the user the indication of the at least one effect on the at least a portion of the anatomical atlas.

9. The system of claim 8, comprising:
- a stimulation output circuit configured to generate the first neurostimulation waveform to be delivered by an implantable medical device to an anatomical target of a patient.

10. The system of claim 8, wherein the user interface configured to display to the user the indication of the at least one effect on the at least a portion of the anatomical atlas is configured to:
- display to the user a graphical representation of an affected region of the anatomical atlas.

11. The system of claim 8, wherein the user interface configured to display to the user the indication of the at least one effect on the at least a portion of the anatomical atlas is configured to:
- display to the user an indication of at least one type of nerve fiber affected.

12. The system of claim 8, wherein the user interface configured to receive user input that at least partially defines a first neurostimulation waveform with at least one of differing pulses and differing pulse intervals is configured to:
- receive user input that defines at least one of a pulse of the first neurostimulation waveform, at least one pulse interval duration, a pulse group of the first neurostimulation waveform, and a group of pulse groups of the first neurostimulation waveform.

13. The system of claim 8, wherein the at least one received parameter of the first neurostimulation waveform is selected from the group consisting of an amplitude, pulse width, at least one pulse interval duration, frequency, electrode configurations, total charge injected per unit time, duty cycling, pulse shape, number of phases, phase order, interphase time, charge balance, and ramping.

14. The system of claim 8, wherein the at least one received parameter includes two or more received parameters, and
- wherein the user interface is configured to receive user input that selects a subset of the two or more received parameters of the first neurostimulation waveform to compare to a corresponding subset of the two or more received parameters of the at least one second neurostimulation waveform stored in the memory.

15. A computer-readable medium comprising instructions that, when executed, cause at least one controller to:
- receive user input that at least partially defines a first neurostimulation waveform with at least one of differing pulses and differing pulse intervals, the user input including at least one received parameter of the first neurostimulation waveform;
- compare the at least one received parameter of the first neurostimulation waveform to a corresponding at least one parameter of at least one second neurostimulation waveform stored in a memory;
- generate and display to the user an indication of a similarity between the compared parameters;
- apply a simulation of the first neurostimulation waveform using at least two pre-selected virtual electrodes to at least a portion of an anatomical atlas; and
- generate to a user an indication of at least one effect on the at least a portion of the anatomical atlas.

16. The computer-readable medium of claim 15, comprising instructions that, when executed, cause the at least one controller to display a graphical representation of an affected region of the anatomical atlas.

17. The computer-readable medium of claim 15, comprising instructions that, when executed, cause the at least one controller to display an indication of at least one type of nerve fiber affected.

18. The computer-readable medium of claim 15, comprising instructions that, when executed, cause the at least one controller to receive user input that defines at least one of a pulse of the first neurostimulation waveform, at least one pulse interval duration, a pulse group of the first neurostimulation waveform, and a group of pulse groups of the first neurostimulation waveform.

19. The computer-readable medium of claim 15, wherein the at least one received parameter of the first neurostimulation waveform is selected from the group consisting of an amplitude, pulse width, at least one pulse interval duration, frequency, electrode configurations, total charge injected per unit time, duty cycling, pulse shape, number of phases, phase order, interphase time, charge balance, and ramping.

20. The computer-readable medium of claim 15, wherein the at least one received parameter includes two or more received parameters, the method comprising:
- receiving user input that selects a subset of the two or more received parameters of the first neurostimulation waveform to compare to a corresponding subset of the two or more received parameters of the at least one second neurostimulation waveform stored in the memory.

* * * * *